United States Patent [19]

Johnson

[11] Patent Number: 4,925,627

[45] Date of Patent: May 15, 1990

[54] OIL SAMPLING DEVICE

[76] Inventor: Gerald K. Johnson, 12908 Valleywood Dr., Woodbridge, Va. 22193

[21] Appl. No.: 144,138

[22] Filed: Jan. 15, 1988

[51] Int. Cl.$^5$ .............................................. B67C 3/16
[52] U.S. Cl. ........................................ 422/99; 422/56; 422/61; 422/100; 73/864.52; 73/863.81; 73/863.82; 73/863.83
[58] Field of Search ........... 73/864.52, 863.81, 863.82, 73/863.83, 863.84; 141/37, 329, 330; 422/55, 56, 58, 61, 100, 88, 99; 436/60, 139, 178, 180; 128/764, 768, 771; 604/148, 140, 318, 404, 414, 415

[56] References Cited

U.S. PATENT DOCUMENTS

| | | | |
|---|---|---|---|
| 4,079,729 | 3/1978 | Cornell | 128/764 |
| 4,154,229 | 5/1979 | Nugent | 128/764 |
| 4,168,699 | 9/1979 | Hauser | 128/768 |
| 4,230,664 | 10/1980 | Cais | 422/61 |
| 4,288,402 | 9/1981 | Ellis | 422/61 |
| 4,548,088 | 10/1985 | Hood, Jr. | 73/864.34 |
| 4,570,685 | 2/1986 | Taylor | 73/864.52 |
| 4,686,192 | 8/1987 | Fisher | 436/60 |

FOREIGN PATENT DOCUMENTS 2025065  1/1980  United Kingdom ............... 128/771

Primary Examiner—Christine M. Nucker
Assistant Examiner—Gregory R. Muir
Attorney, Agent, or Firm—John C. Smith, Jr.

[57] ABSTRACT

A device for conveniently sampling and testing oil from the crankcase of an internal combustion engine comprises a tubular member, installed in the dipstick guide tube of the internal combustion engine and having a chamber above the guide tube inlet, and a vacuum filled sample receptacle having a seal which, when the receptacle is inserted in the chamber, is opened causing oil from the crankcase to be drawn into the receptacle. When the receptacle is withdrawn from the chamber the seal automatically closes, providing a convenient container for the oil sample to be sent to a laboratory for analysis. Optionally, to test the oil for acidity at the time the sample is received in the receptacle, the receptacle may contain a reagent which will indicate by color the pH of the oil sample.

11 Claims, 1 Drawing Sheet

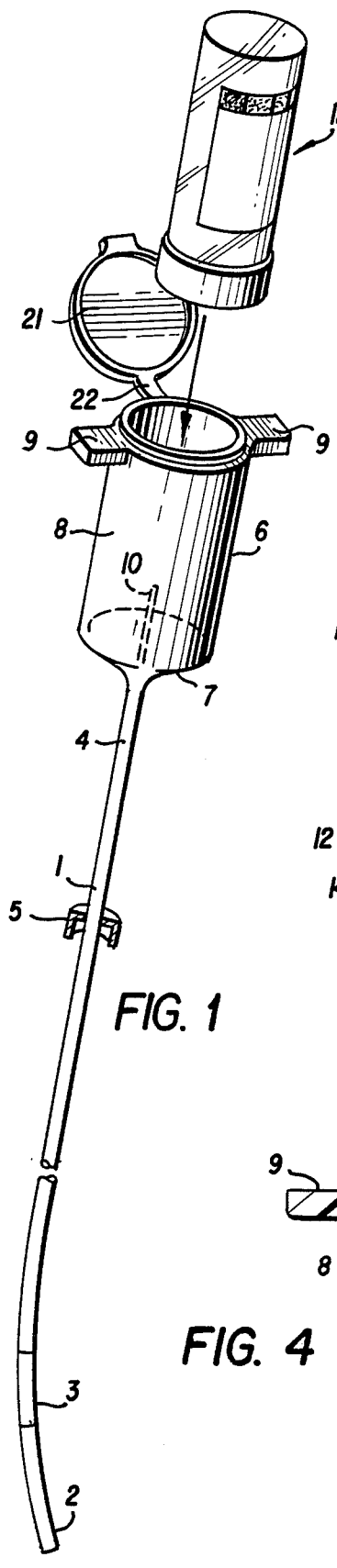
FIG. 1
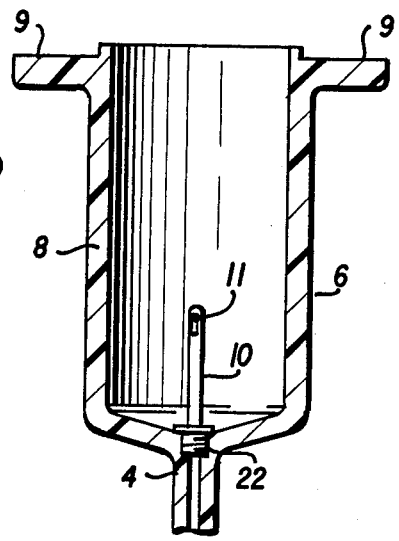
FIG. 2
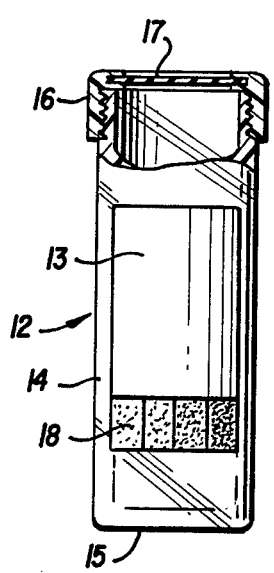
FIG. 3
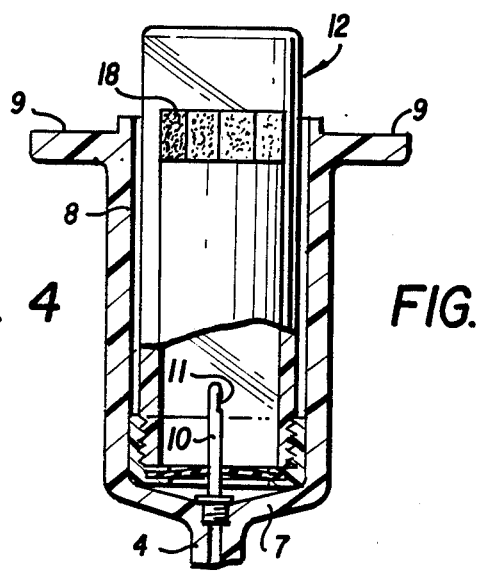
FIG. 4
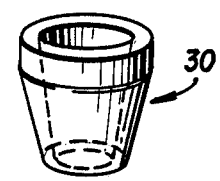
FIG. 5
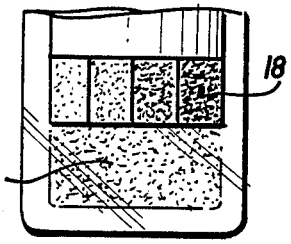
FIG. 6
FIG. 7

OIL SAMPLING DEVICE

BACKGROUND OF THE INVENTION

The heavy equipment and transportation industries have long had need for a methodology to determine the internal condition and need for service of the crucial large engines that are used in fixed plant, maritime, railroad, construction and aircraft applications. The expense of these engines and the high opportunity costs incurred in shutting them down for maintenance gives rise to the need for a preventive maintenance method to accurately determine when an engine requires service and to predict incipient failures.

The railroad industry discovered infrared spectrometry and atomic absorption spectrometry as a means of monitoring wear of internal engine components in the 1940's. Since that time these principles have been adopted by most industries that use large or expensive oil wetted components. Oil companies and most engine manufacturers have some type of oil analysis program that they offer to their customers. The common element of all present systems is a lack of perceived value to the person who has the most critical role in the system, the operator. The systems are failures because they are too messy and complicated with no immediate direct return to the operators, and thus the operators have no incentive to reliably participate in the systems.

U.S. Pat. No. 4,203,725 to Snowden, Jr. et al discloses apparatus for testing lubricating oil; but, like other prior art systems, this system does not provide means for cleanly withdrawing an oil sample from the engine and transferring it to a container for testing.

This invention relates to an oil sampling device designed to provide a simple and clean means for removing and providing for analysis a sample of oil from an engine crankcase or oil sump. Given the economic advantages of preventive maintenance, there exists a need for vehicle owners and operators to be able to remove and analyze easily and effectively the oil in an engine crankcase. The device of the present invention provides not only the function of checking the level of oil in the engine crankcase, which is performed by conventional dipsticks, but also permits the removal of a sample of oil from the crankcase to analyze the composition of the oil. This analysis of the composition of the oil supplies the owner with information concerning oil conditions and also serves as an indication of engine performance and present and future maintenance requirements. The ability to quickly and cleanly generate such information allows the vehicle owner or operator to avoid the time and expense required for servicing the vehicle unnecessarily while at the same time supplying the engine performance analysis information needed to maintain safe and efficient operation of the vehicle.

Analysis of the oil sampled by the device of the present invention is performed based on known scientific principles of internal combustion engines. Motor oil used in internal combustion engines is naturally basic. It becomes acidic with use and at that time begins to corrode engine components. It is therefore important to be able to check the pH level of engine oil, its total base number reserve (TBN reserve) to determine the best time to change the oil prior to its base reserve being depleted. It is normal practice to change the oil when its TBN reserve dips below fifty percent of its original level.

In addition to testing the pH of the oil sample generated by the apparatus of the present invention, the oil sample can be further analyzed through infrared spectroscopy and other diagnostic techniques. In this manner, metallic particles and other contaminants can be detected and measured to thereby indicate engine wear rates and trends, cooling and fuel system leaks, air cleaner problems, etc. Combustion problems in the engine can also be detected through various analysis techniques of oil samples generated by the present invention.

Accordingly, it is an object of the present invention to provide an oil sampling device which is easy to use and is clean and by which no oil is introduced into the environment or onto the hands or clothes of the person obtaining the oil sample.

Accordingly, it is another object of the present invention to provide an oil sampling system which permits the operator of a motor vehicle, for example, the operator of a truck, to perform a simple, clean sampling of the oil, to obtain an efficient analysis of the sample for any immediate problem conditions and to provide for efficient analysis of the oil sample to indicate engine performance.

It is a further object of the present invention to provide an apparatus by which an oil sample can be generated and analyzed to produce information for the vehicle operator as to when engine oil should be changed and what engine maintenance, if any, is required.

It is a still further object of the present invention to provide a device by which an oil sample is generated and the sample easily handled and transported for subsequent analysis of the oil.

These and other objects of the invention will become apparent in the following description in connection with the accompanying drawings.

SUMMARY OF THE INVENTION

These and other objects have been achieved by the present invention by providing an oil sampling device by which an operator can cleanly and efficiently remove a sample of oil from a crankcase of, for example, construction equipment. The oil sampling device of the present invention comprises a hollow, flexible tube which is inserted into a passage extending from the crankcase of the engine. The end of the hollow tube is immersed in the oil supply of the crankcase or oil sump. At the other end of the tube is connected a top portion having a handle thereon by which the operator may insert and remove the device from the crankcase of the engine. Between the hollow tube and the top portion is provided a valve which extends into a cavity provided in the top portion. Into this cavity may be inserted an evacuated sample receptacle having a self-sealing end portion. When the self-sealing end portion of the sample receptacle contacts the valve, the end is pierced by the valve. The vacuum in the sample receptacle then functions to suck oil from the engine crankcase through the tube and valve and into the sample receptacle. The sample receptacle may be removed from contact with the valve thus removing the suction from the oil supply. The oil in the tube then drains back through the tube into the crankcase.

The sample thus obtained may then be analyzed to generate diagnostic information indicative of the operation of the engine and maintenance requirements. Particularly, the sample receptacle may be provided with a pH indicating means to give the operator an immediate indication as to the TBN reserve, the degree to which the oil has become acidic and therefore requires change. In addition, the sample of oil may be further analyzed by infrared spectroscopy techniques, ferrography, spatter and/or blotter tests or the like.

BRIEF DESCRIPTION OF THE DRAWINGS

The objects of the present invention will become clear after review of the description of the invention taken in conjunction with the drawings wherein:

FIG. 1 is a perspective view of an oil sampling device of the present invention including a sample receptacle for insertion in an upper portion thereof;

FIG. 2 is a side view, partly in cross-section, of the chamber of the oil sampling device of FIG. 1;

FIG. 3 is a side view, partly in cross-section, of the closed, vacuum-filled sample receptacle shown in FIG. 1.

FIG. 4 is a side view, partly in cross-section, of the closed vacuum-filled sample receptacle shown in FIG. 3 located in operative position in the chamber shown in FIG. 2;

FIG. 5 is a side view, partly in cross-section, of the upper portion of a further embodiment of a closed, vacuum-filled sample receptacle;

FIG. 6 is an enlarged side view of the lower portion of the closed, vacuum-filled sample receptacle of FIG. 3; and FIG. 7 is a perspective view of an adaptor for the dipstick guide tube of an internal combustion engine.

DESCRIPTION OF THE PREFERRED EMBODIMENT

Referring to the drawings and particularly FIG. 1, the oil sampling device of the present invention comprises a flexible hollow tube 1, adapted to be inserted into a tubular guide extending upwardly from the crankcase of an internal combustion engine. The tube may be made of a heat-resistant plastic or the like. The tube 1 is inserted into the guide such that the lower end 2 of the tube is immersed in oil located in the crankcase. An oil level indicator 3 is provided near the lower end of the tube 1. This oil level indicator comprises a graduated scale on the outer surface of the tube. The graduation marks are labeled according to the length of the tube and the size of the crankcase so that the level to which the oil comes on the scale gives the operator an accurate indication of the amount of oil in the crankcase.

Near the upper end 14 of the tube 1 is provided a retainer 5 for retaining the oil sampling device in position in the guide tube extending from the crankcase of the engine. When the oil sampling device is inserted into the guide tube, the retainer 5 fits over the upper end of the guide to prevent the oil sampling device from being dislodged from the guide tube during operation of the engine and to prevent oil from spilling out of the upper portion of the guide tube.

At the upper end 4 of the tube 1 is an open-ended chamber 6 formed by a conical base 7 and vertical walls 8 extending upwardly from the conical base. The chamber 6 may be integrally formed with the tube 1 of plastic. For convenience, handles 9 are integrally formed with the sidewalls near the top thereof to provide means for the operator of the oil sampling device to hold the device while inserting and removing the device from the guide tube leading to the crank case.

A hollow needle 10 projects upwardly from the center of the conical base 7 of the chamber 6 and provides fluid communication from the tube 1 to the chamber 6. A hole 11 is provided adjacent the end of the needle 10 so that oil may pass from the tube 1 through the needle 10 and out through the hole 11. The needle 10 has an externally threaded base 27 which is secured in a corresponding internally threaded cavity in the base 7 of the chamber 6.

A removable cap 21, connected by a flexible strap 22 to the upper end of a vertical wall 8, covers the open end of chamber 6 to protect the chamber from dirt when the chamber is not in use.

An evacuated sample container 12 is provided for receiving a quantity of fluid from the tube 1 through the needle 10. The container 12 comprises an evacuated cavity 13 enclosed by sides 14, a bottom 15 and a screw cap 16 secured to the sides. The end of the cap 16 comprises a self-sealing material 17 such as a rubber film material. The cap 16 is removable from the container 12 in order to provide access to the oil after it has been collected in the container. When the operator of the device desires to remove a sample of oil from the crankcase, the cap 21 is removed from the chamber 6 and the sample container 12 is inserted, cap 16 first, into the chamber. When the self-sealing material 17 contacts the needle 10, it is pierced by the needle resulting in the hole 11 of the needle 10 being located within the evacuated cavity 13 (see FIG. 4). As the sample container 12 is further inserted into the chamber 6, the cap 16 rests upon the conical base 7 of the chamber 6. The piercing of the self-sealing material by the needle 10 and the resultant placement of the hole 11 within the vacuum-filled cavity 13 renders the cavity in fluid communication with the passageway of the tube 1. As a result, the vacuum in the cavity sucks air from the passageway of the tube 1 through the needle 10 into the cavity 13. This suction in the tube results in oil from the crankcase being lifted from the crankcase, through the passageway in the tube 1 into the cavity 13. When a quantity of oil sufficient for analysis purposes has been gathered in the sample container 12, the sample container is removed from the chamber 6. Because the end of the cap 16 is made of a self-sealing material 17, no oil will leak from the sample container 12 after its removal from the piercing needle 10. Thus, an adequate supply of oil, such as about 10 milliliters, may be cleanly and efficiently removed from the crankcase of the engine.

Once a sample of oil has been collected in the above-described manner, the oil may then be analyzed to gather information indicative of engine performance and maintenance requirements. According to one embodiment of the present invention, the evacuated cavity 13 of the sample container 12 contains a pH indicating means therein such as a pH indicative reagent. When the oil drawn into the chamber contacts and is mixed with the pH indicative reagent, the resultant color of the reagent is indicative of the pH of the oil. Thus, by forming the side 14 of the sample container from a transparent material, the operator may visually inspect the color of the reagent to determine the pH of the oil. A legend in the form of a color-coded paper strip 18 may be located on the side of the sample container to provide comparison means so that the operator can compare the color of the reagent with the legend to determine the pH of the oil. If the oil is found to be acidic, the operator is immediately given a visual indication of this fact and is thereby advised that the oil should be changed. If the oil is neutral or alkaline, the oil does not need to be changed.

According to an alternative embodiment of the invention, located within the cap 16 is a compartment or plastic pillow 19 containing a pH indicative reagent. Upon insertion of the sample container 12 into the chamber 6, the needle 10 pierces both the self-sealing film 17 and the container or pillow 19, after which the oil is drawn by the vacuum in the container 12 into the cavity 13 where the oil is mixed with the reagent. As the reagent in the chamber or pillow 19 reacts with the oil, the reagent changes color and the resultant color, shown at 20 in FIG. 6, is indicative of the pH of the oil. The legend 18 gives the operator an immediate visual indication of the pH of the oil. Accordingly, the operator can determine whether the oil has become acidic and therefore needs to be changed.

A specific example of a suitable reagent is a water solution of the sodium salt of bromothymol blue which is maintained in an air-free environment in a plastic film pillow until borken by the needle. The color of the bromothymol blue changes in the pH range of 5.0–8.0, the range motor oil goes through from the time it is fresh until the time it must be changed. The reagent accumulates in the bottom 20 of the sample container 12. A green color indicates the total alkaline reserve of the oil has not changed pH more than two points. Yellow indicates the neutral range, and bright orange indicates acidity.

If a laboratory analysis of the oil is required, a second sample of the oil may be taken using a sample container 12 which does not contain a pH indicative reagent. This oil sample may then be sent to a laboratory where technicians can determine details of engine performance. Specifically, the presence of metal shavings in the oil may be indicative of abnormal engine wear. The presence of glycol or water in the oil may be indicative of cooling system leaks. In addition, such analysis may reveal fuel system trouble and abnormal degradation according to the specific principles of the characteristics of internal combustion engines.

The oil sample device of the present invention can, of course, be used as a conventional dipstick. To check the level of oil in the engine crankcase, the operator simply chooses not to insert the sample container 12 in the chamber 6. An operator need only pull the handles 9 to remove the oil sample device from the guide tube of the engine and read the level of oil in the level indicator 2. If visual inspection of the oil on the indicator 2 indicates that the oil appears dirty and may therefore need to be changed, the operator may simply reinsert the oil sample device into the crankcase guide, open the cap 21 from the top of the device and insert the sample container 12 into the chamber 6. Because of the vacuum contained in the cavity 13, oil from the crankcase is drawn into the sample container 12 as described above. When the sample has been collected, the operator removes the sample container 12 from the chamber 6 and closes the cap 21 to protect the chamber 6.

FIG. 7 shows an adaptor which, optionally, may be used with the oil sampling device of the present invention. The adaptor 30 is a tubular member for insertion in the open end of the guide tube of the engine. The lower external wall of the adaptor is tapered such that the adaptor may be accommodated in guide tubes of different internal diameters. With the adaptor permanently positioned in the end of the guide tube of the engine, a secure fit between the upper portion of the adaptor and the retainer 5 of the oil sampling device is assured.

While it is apparent that the principles of the invention are well calculated to fulfill the above-stated objects, it will be understood that the invention is subject to modification, variation and change without departing from the proper spirit or scope of the invention as defined in the appended claims.

I claim:

1. An oil sampling device adapted for insertion through a tubular guide into the crankcase of an internal combustion engine to remove an oil sample from said crankcase, comprising:
   (a) an elongated hollow tube having opposite first and seconds end sand a passageway connecting said first and second ends, said hollow tube being adapted to be inserted through a tubular guide in an internal combustion engine with said first end immersed in oil in the crankcase of said engine;
   (b) means defining a chamber having a lower end, said walls and an open end, said lower end being connected to said second end of said hollow tube such that said passageway of said tube communicates with said chamber;
   (c) valve actuating means in said chamber; and
   (d) means defining a closed, vacuum filled sample receptacle for insertion into and withdrawal from said chamber through said open end thereof, said sample receptacle comprising valve means arranged to be automatically opened by said valve actuating means when said sample receptacle is inserted in said chamber to connect said passageway in said tube with said sample receptacle and to be automatically closed when said sample receptacle is withdrawn from said chamber; whereby a sample of oil may be drawn by vacuum from said crankcase of said engine, when said vacuum filled sample receptacle is inserted in said chamber and said first end of said hollow tube is immersed in said oil, through said passageway in said tube and into said sample receptacle.

2. An oil sampling device according to claim 1 wherein said valve actuating means comprises a hollow needle projecting upwardly within said chamber from said lower end thereof and communicating with said passageway in said hollow tube, and said valve means in said sample receptacle comprises a self-sealing wall portion of said sample receptacle arranged to be pierced by said hollow needle when said sample receptacle is inserted in said chamber and to reseal when said sample receptacle is withdrawn from said chamber.

3. An oil sampling device according to claim 1 wherein said sample receptacle comprises pH indicating means for indicating the pH of oil therein.

4. An oil sampling device according to claim 3 further comprising frangible container means for said pH indicating means, said container means being arranged in said sample receptacle to be pierced by said hollow needle when said sample receptacle is inserted in said chamber.

5. An oil sampling device according to claim 1 wherein said elongated hollow tube comprises a graduated scale on said tube for indicating the level of oil in said crankcase.

6. An oil sampling device according to claim 2 wherein said sample receptacle is transparent.

7. An oil sampling device according to claim 1 wherein said elongated hollow tube is flexible.

8. An oil sampling device according to claim 7 wherein said elongated hollow tube comprises a plastic material.

9. An oil sampling device according to claim 1 further comprising a protective cap hingedly attached to said means defining a chamber, for closing said open end of said chamber.

10. An oil sampling device according to claim 7 wherein said elongated hollow tube and said means defining a chamber are formed integrally as a single piece from plastic material.

11. An oil sampling device according to claim 10 wherein said hollow needle includes a base end and a pointed end, said base end of said needle and said lower end of said chamber having cooperating means for securing said base end of said needle in place in said lower end of said chamber such that said hollow needle communicates with said passageway in said hollow tube.

* * * * *